United States Patent
Cohen et al.

(10) Patent No.: US 7,853,036 B2
(45) Date of Patent: Dec. 14, 2010

(54) SYSTEM AND METHOD FOR USING A DIGITAL WATERMARK ON A GRAPHICAL USER INTERFACE AS IDENTIFYING INDICIA IN A HEALTHCARE SETTING

(75) Inventors: Stuart Mark Cohen, Phoenix, AZ (US); Douglas Michael Saus, Platte City, MO (US); Carrie Jeanne Vanzant, Pleasant Valley, MO (US); Russell William Webb, Lawrence, KS (US); Kevin John Winkel, Gladstone, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1034 days.

(21) Appl. No.: 11/610,817

(22) Filed: Dec. 14, 2006

(65) Prior Publication Data
US 2008/0010592 A1    Jan. 10, 2008

Related U.S. Application Data

(63) Continuation of application No. 10/447,556, filed on May 29, 2003, now Pat. No. 7,274,799.

(51) Int. Cl.
*G06K 9/00*    (2006.01)
(52) U.S. Cl. ..................... 382/100; 713/176

(58) Field of Classification Search ............... 382/100, 382/232; 380/54, 210, 252, 287; 713/176; 704/200.1, 273; 381/73.1; 348/460, 463
See application file for complete search history.

(56) References Cited

U.S. PATENT DOCUMENTS

| | | |
|---|---|---|
| 6,098,084 A | 8/2000 | Mori |
| 6,563,936 B2 | 5/2003 | Brill et al. |
| 6,590,996 B1 | 7/2003 | Reed et al. |
| 6,636,248 B1 | 10/2003 | Christensen et al. |
| 7,050,603 B2 | 5/2006 | Rhoads et al. |
| 7,494,045 B2 * | 2/2009 | Menhardt et al. ........... 235/375 |
| 2002/0059520 A1 | 5/2002 | Murakami et al. |
| 2003/0038820 A1 | 2/2003 | Purpura |

* cited by examiner

*Primary Examiner*—Anand Bhatnagar
(74) *Attorney, Agent, or Firm*—Shook, Hardy & Bacon L.L.P.

(57) ABSTRACT

A method for use in a computer system is provided that links a patient with patient-related data that is displayed on a graphical user interface. The method includes first determining if a digital watermark is required. If a digital watermark is required, the current background color for the display of patient-related data is obtained, along with an intensity value. The subject matter for the watermark is also obtained. The color of the digital watermark is calculated, based upon the obtained background color and intensity value. The digital watermark is then rendered on the display.

16 Claims, 6 Drawing Sheets

SYSTEM AND METHOD FOR USING A DIGITAL WATERMARK ON A GRAPHICAL USER INTERFACE AS IDENTIFYING INDICIA IN A HEALTHCARE SETTING

CROSS-REFERENCE TO RELATED APPLICATIONS

This application is a continuation of U.S. patent application Ser. No. 10/447,556, filed May 29, 2003, the disclosure of which is hereby incorporated herein by reference in its entirety.

STATEMENT REGARDING FEDERALLY SPONSORED RESEARCH OR DEVELOPMENT

Not applicable.

TECHNICAL FIELD

The present invention relates generally to the field of computer software. More particularly, the invention relates to a computerized system and method for providing a digital watermark on a graphical user interface as an identifier within a healthcare setting.

BACKGROUND OF THE INVENTION

The use of computers within the healthcare industry is becoming common practice. Computer systems are now being used throughout the healthcare industry for a number of different purposes. Some computer operating systems include a graphical user interface (GUI), described generally as a graphical operating system, which displays various information to the user as a combination of pictures and text that the user can manipulate. Generally, some graphical operating systems instigate an instance of a software application by displaying the various text, graphics and features of the application within a rectangular window on the visual display. Increasingly, information is displayed to healthcare providers on these visual displays, or graphical user interfaces. These displays are typically monitors associated with a computer or computer network.

One drawback in the use of these displays is the limited amount of available screen space. The available screen space is often referred to as "screen real estate." This screen real estate is valuable and must be put to good use. In other words, it is desirable to efficiently and effectively use the screen real estate. The display of information must be viewable from a reasonable distance, must place the information in a proper context (e.g. identify the information with the respective patient in some way) and present a sufficient amount of information within a single screen. The last consideration is sometimes referred to as a dense patient view. One method of placing the information in the proper context is to display the patient name or other identifier in a field on the screen, along with the relevant patient data.

One drawback in this method is the use of valuable screen real estate in the display of the patient name or identifier. Another drawback of this method relates to the different settings in which the information is viewed and used. The display of patient information can occur in many different settings. For example, the display may be in a publicly-viewable area or in a more secured area, such as an operating room. The display of patient information in a publicly-viewable area presents the challenge of displaying meaningful patient data, in context, without divulging personal information of the patient. If the patient name is displayed along with the patient data, this goal is not achieved.

Accordingly, there is a need for a more efficient system and method for utilizing screen real estate to display patient information in context. There is also a need for a system and method for displaying patient information in a publicly viewable area in a manner that places the information in context and simultaneously protects the privacy interests of the patient.

SUMMARY OF THE INVENTION

The present invention overcomes the drawbacks of the prior art mentioned above. In one aspect of the present invention, a method for use in a computer system is provided that links a patient with patient-related data that is displayed on a graphical user interface. The method includes first determining if a digital watermark is required. If a digital watermark is required, the current background color for the display of patient-related data is obtained, along with an intensity value. The subject matter for the watermark is also obtained. The color of the digital watermark is calculated, based upon the obtained background color and intensity value. The digital watermark is then rendered on the display.

BRIEF DESCRIPTION OF THE DRAWING FIGURES

The present invention is described in detail below with reference to the attached drawing figures, wherein.

DETAILED DESCRIPTION OF THE INVENTION

Figure 1:
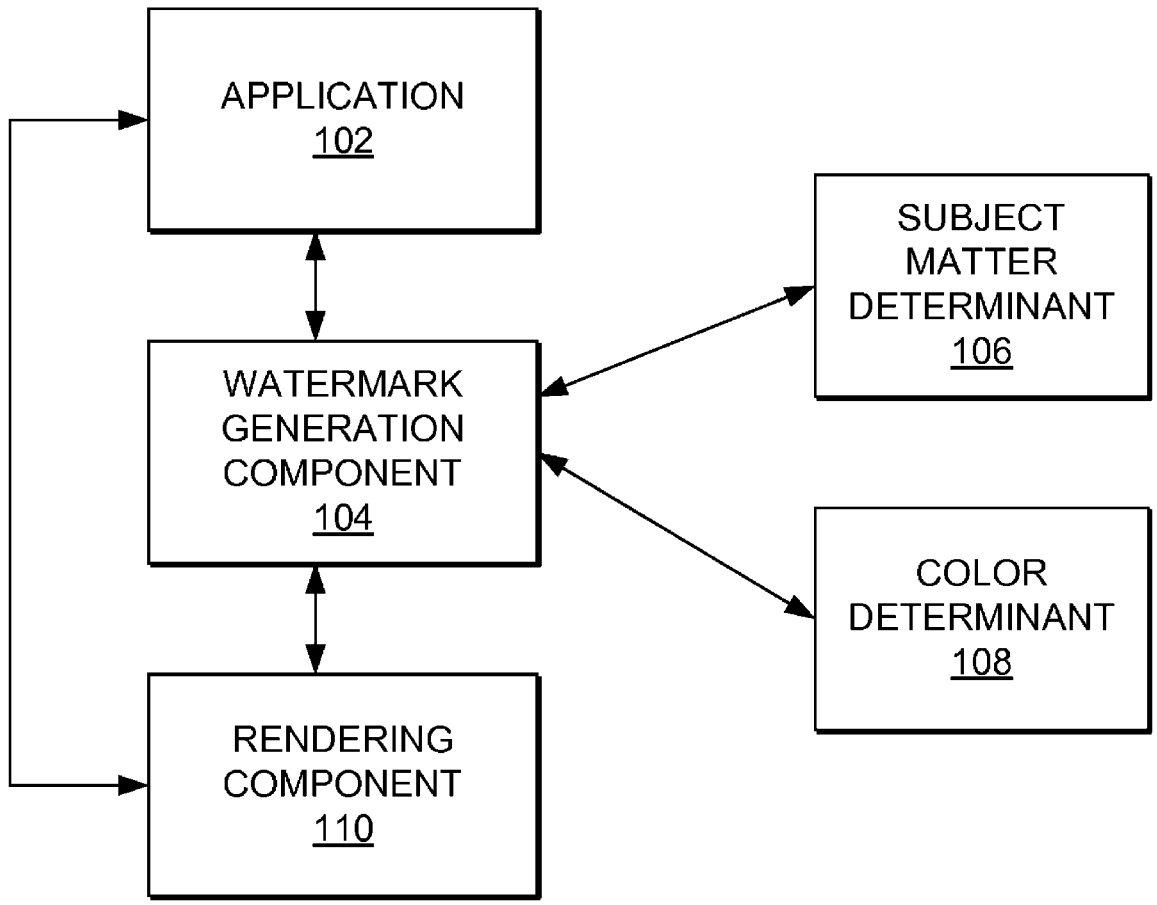
FIG. 1 is a block diagram of a computing system including a watermark generation component in accordance with a preferred embodiment of the present invention.

The present invention is directed to a system and method that displays a digital watermark for use as an identifier on a graphical user interface within a healthcare setting. FIG. 1 depicts an exemplary computer system 100 for displaying healthcare-related information in accordance with the present invention.

The system 100 includes a software application component 102. The application 102 can be any of a variety of healthcare-related software applications. The application 102 is in communication with a watermark generation component 104. Component 104 provides the desired digital watermark to the application 102. It should be understood that component 104 may be provided as a part of application 102, or may be provided as a separate software package. Generation component 104 includes a subject matter determinant 106 and a color determinant 108. Subject matter determinant 106 obtains the text or other identifier that is to be used and displayed as the digital watermark. The identifier can be any of a number of fields that provide a connection between the healthcare-related information and the patient. For example, the identifier can be the patient name, the medical record number (MRN), or the location of the patient. The identifier used may also depend on the setting in which the information is displayed. Typically, in publicly viewable areas, the patient name would not be a desirable identifier.

Subject matter determinant 106 obtains the identifier to be displayed. The identifier is preferably configurable by the user, such that the user can select the desired field to be used as the digital watermark. For example, the user may be provided with a number of possible field options for the identifier. These options can be provided in a drop-down menu, or as radio buttons, or in any user-selected user interface display. Subject matter determinant 106 also preferably allows the user the option of cycling on a time basis through a set number of different watermark identifiers. Color determinant 108 provides the color to be used for the watermark identifier, as is more fully described below. The subject matter and color for the watermark identifier are then passed to a rendering component 110, which renders the watermark identifier on the display.

The present invention and its components may be implemented in a variety of computing system environments. For example, each of the components and subcomponents of the computer system 100 may be embodied in an application program running on one or more personal computers (PCs). This computing system environment is only one example of a suitable computing environment and is not intended to suggest any limitation as to the scope of use or functionality of the invention. The invention may also be implemented with numerous other general purpose or special purpose computing system environments or configurations. Examples of other well-known computing systems, environments, and/or configurations that may be suitable for use with the invention include, but are not limited to, server computers, hand-held or laptop devices, multiprocessor systems, microprocessor-based systems, programmable consumer electronics, network PCs, minicomputers, mainframe computers, distributed computing environments that include any of the above systems or devices, and the like.

The invention may be described in the general context of computer-executable instructions, such as program modules. Generally, program modules include routines, programs, objects, components, segments, schemas, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Computers typically include a variety of computer-readable media. Computer-readable media includes any media that can be accessed by a computer and includes both volatile and nonvolatile media, removable and non-removable media. By way of example, and not limitation, computer-readable media may comprise computer storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD), holographic or other optical storage, magnetic cassettes, magnetic tape, magnetic disk storage or other magnetic storage devices, or any other medium which can be used to store the desired information and which can be accessed by a computer.

Communications media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communications media includes wired media such as a wired network or direct wired connection, and wireless media such as acoustic, RF, infrared, spread spectrum and other wireless media. Communications media are commonly used to upload and download information in a network environment, such as the Internet. Combinations of any of the above should also be included within the scope of computer-readable media.

The computer may operate in a networked environment using logical connections to one or more remote computers, such as a personal computer, a server, a router, a network PC, a peer device or other common network node, and typically includes many or all of the elements described above. The logical connections may include connections to a local area network (LAN), a wide area network (WAN) and/or other networks. Such networking environments are commonplace in offices, enterprise-wide computer networks, intranets and the Internet.

Computer storage mechanisms and associated media provide storage of computer-readable instructions, data structures, program modules and other data for the computer. A user may enter commands and information into the computer through input devices such as a keyboard and pointing device, commonly referred to as a mouse, trackball or touch pad. Other input devices may include a microphone, touchscreen, camera, joystick, game pad, scanner, or the like. In addition to a monitor or other type of display device, computers may also include other peripheral output devices such as speakers and printers, which may be connected through an output peripheral interface.

Although many other internal components of computers have not been discussed herein, those of ordinary skill in the art will appreciate that such components and their interconnection are well-known. Accordingly, additional details concerning the internal construction of computers need not be disclosed in connection with the present invention.

Figure 2:
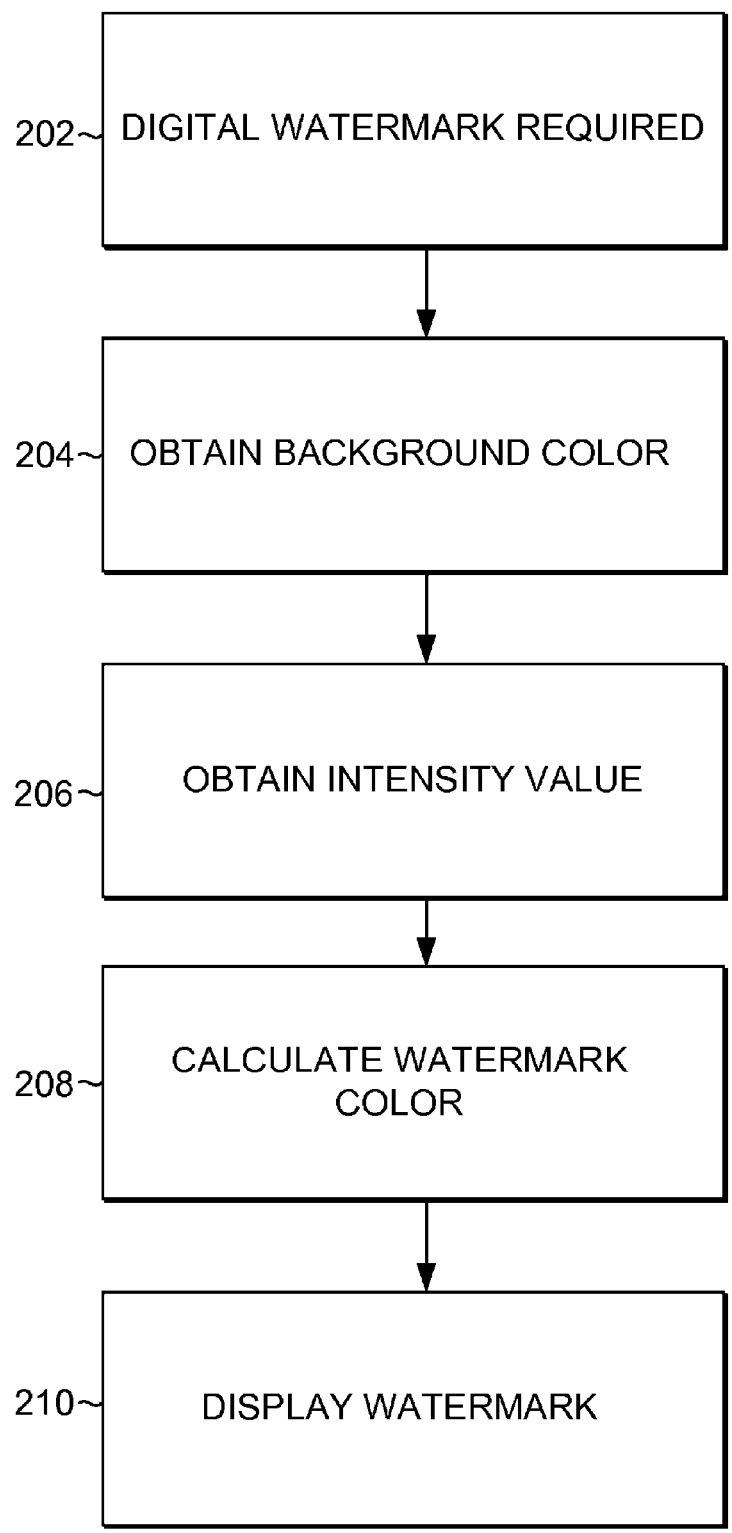
FIG. 2 is a flowchart representative of a computer program for displaying a digital watermark in a healthcare setting in accordance with a preferred embodiment of the present invention.

The components of FIG. 1 are used to execute the method, as shown in FIG. 2 and as described below. With reference to FIG. 2, the method begins with an application that requires a digital watermark, as shown at 202. When an application requires a digital watermark, the method continues by obtaining the current background color, as shown at 204. The background color is used as one factor in determining the rendering parameters for the digital watermark. As shown at 206, an intensity value is also obtained for the digital watermark. The intensity value may be set to a default value, or may be user-provided. Preferably, the intensity value passed in is an integer between zero and one hundred. The intensity value is another factor in determining the rendering parameters for the digital watermark. The method continues by passing in the current background color and the intensity value to a function, which calculates the color for the digital watermark, as shown at 208. The returned color is then used by the rendering component 110 (FIG. 1) to display the text of the watermark in the calculated color, as shown at 210.

An exemplary function used to determine the watermark color is shown in Table 1 below. It should be understood that this is only one example, shown in Visual Basic nomenclature, and that other methods could be used to calculate or determine the color of the digital watermark. The function takes in the current display background color and an intensity value and returns the watermark color.

TABLE 1

```
'This function will take in the current background color,
and an intensity value between 0 and 100
'The watermark color will be calculated and returned by the function
Public Function GetWaterColor(ByVal lColor As Long, ByVal nIntensity
As Integer) As Long
    Dim lRed As Double
    Dim lGreen As Double
    Dim lBlue As Double
    Dim i As Long
    Dim dHue As Double
    Dim dLum As Double
    Dim dSat As Double
    'Convert the background color to RGB (Red, Green, Blue) values
    lRed = RedFromRGB(lColor)
    lGreen = GreenFromRGB(lColor)
    lBlue = BlueFromRGB(lColor)
    'Convert the RGB values to HLS (Hue, Luminescence, Saturation)
    RgbToHls CDbl(lRed), CDbl(lGreen), CDbl(lBlue), dHue, dLum, dSat
    'Luminescence values range from 0-240, so we will either add or
    subtract the intensity
    'value based on the midpoint of this range
If dLum > 120 Then
    dLum = dLum - nIntensity
Else
    dLum = dLum + nIntensity
End If
'Convert HLS back to RGB
HlsToRgb dHue, dLum, dSat, lRed, lGreen, lBlue
'Ensure that all RGB values are within their valid range
If lRed < 0 Then
    lRed = 0
End If
If lRed > 255 Then
    lRed = 255
End If
If lGreen < 0 Then
    lGreen = 0
End If
If lGreen > 255 Then
    lGreen = 255
End If
If lBlue < 0 Then
    lBlue = 0
End If
If lBlue > 255 Then
    lBlue = 255
End If
    'Set the return value of the function
GetWaterColor = rgb(lRed, lGreen, lBlue)
End Function
```

As shown, the function begins by obtaining the current background color in RGB (red, green, blue) values. These values are then converted to HLS (hue, luminescence, saturation) values. The luminescence values are then compared with the midpoint of the luminescence range. If the luminescence value is greater than the midpoint, the intensity value is subtracted from the luminescence value. If the luminescence value is less than the midpoint, the intensity value is added to the luminescence value. Following the adjustment of the luminescence value, the HLS values are converted back to RGB. After this conversion, a check is made to ensure that the RGB values are within a valid range. The converted RGB values are then returned as the output of the function. These RGB values are used as the watermark color. The function thus obtains the background color and intensity and returns a watermark color with a different luminescence.

Figure 3:
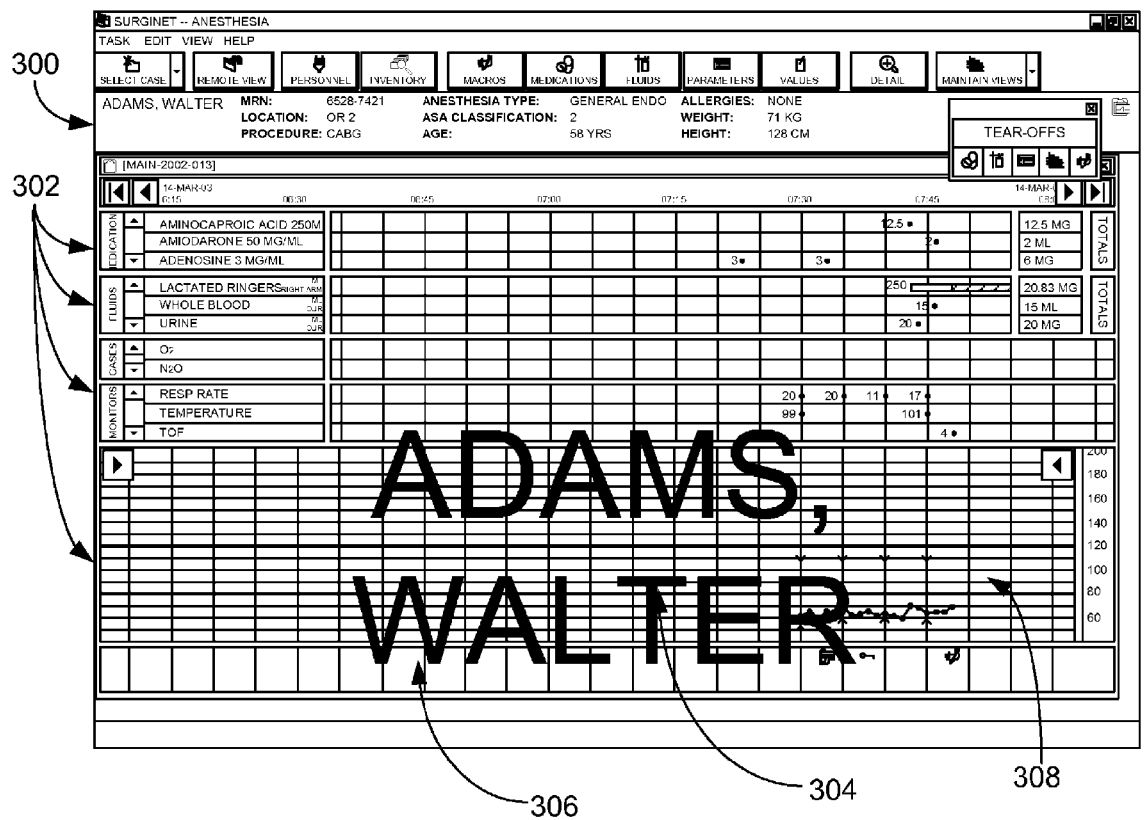
FIGS. 3-6 are screen shots illustrating an exemplary implementation of the digital watermarks with varying intensities and backgrounds.

FIGS. 3-6 are examples of screen shots utilizing the digital watermark identifier. FIG. 3 illustrates a screen shot from a healthcare software user interface. The screen shot of FIG. 3 includes a number of information fields 300. Exemplary fields include patient name, medical record number, patient location and other patient information. Below the information fields 300 are a number of data fields 302, one of which is displayed in a larger viewing window. A patient name is displayed in this larger viewing window as a digital watermark 304. Again, it should be understood that the subject matter of the identifier can vary, and need not always be the patient name. In publicly viewable areas, it is preferable to use another identifier, such as the medical record number. In other instances, the watermark can identify other clinical information such as the physician associated with the information in a particular viewing window.

Figure 4:
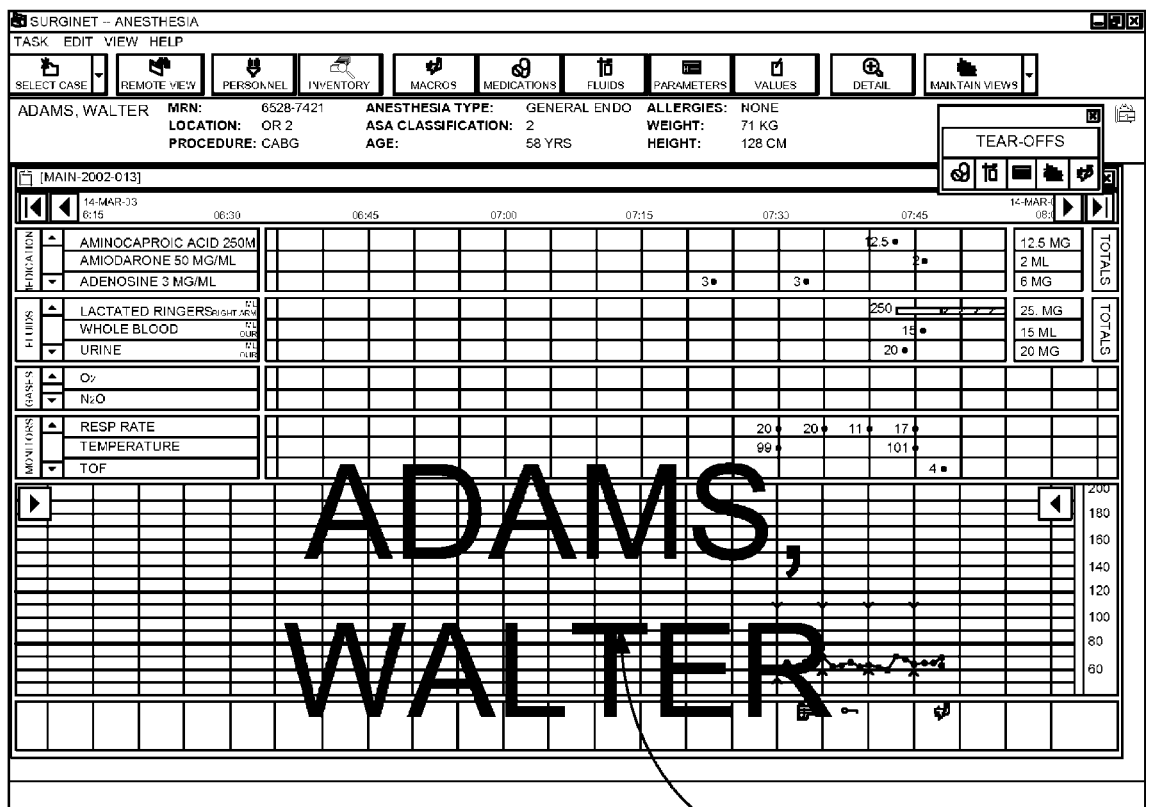
Figure 5:
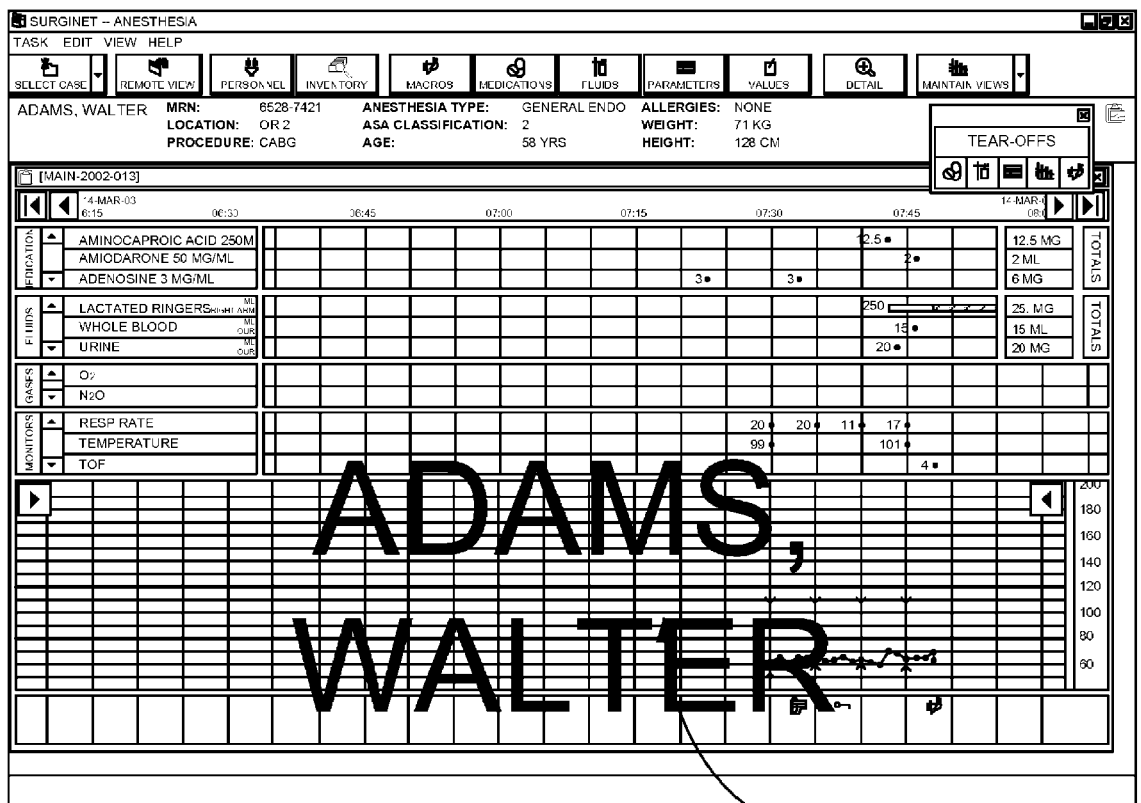

The contrast between the background color 306 and the watermark color 308 is dependent upon the intensity value being used. FIGS. 4 and 5 show the same screen shot as FIG. 3, but with an increased intensity value for the watermark 304. It can therefore be seen that the watermark identifier can be adjusted through adjustments to the intensity values.

Figure 6:
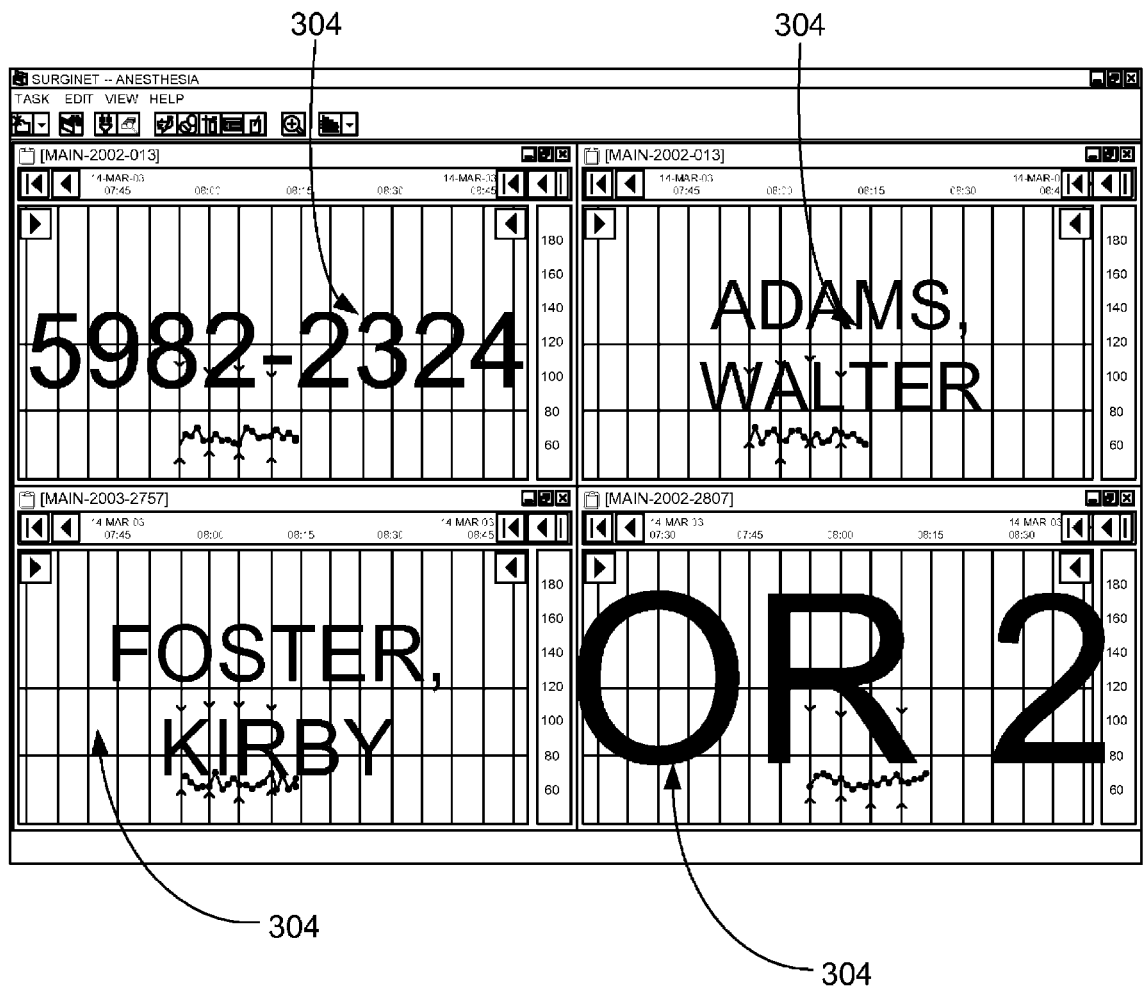

FIG. 6 illustrates the effect of the watermark identifier 304 on displays of different backgrounds. As can be seen, in each instance the watermark identifier is of a color similar to that of the background. Again, the degree to which the watermark "stands out" is determined by the intensity value selected and passed in. FIG. 6 also illustrates watermarks of different subject matter. The top left display illustrates a watermark using a medical record number. The top right and bottom left displays illustrate a watermark using the patient name. The bottom right identifier illustrates a display using the patient location.

Those skilled in the art will appreciate that the present invention represents a significant advancement of the state of the art beyond existing applications, especially with respect to the practical benefits it provides. The present invention allows the displayed information to be associated with a particular patient in a dense view, without sacrificing valuable screen real estate. Moreover, the invention allows this association in publicly viewable areas without sacrificing the privacy of the patient. The system is configurable, and can display different watermark identifiers as the situation warrants. The system is also flexible in that the watermark identifier accommodates displays of any background color and allows the intensity of the watermark identifier to be altered if desired.

Alternative embodiments and implementations of the present invention will become apparent to those skilled in the art to which it pertains upon review of the specification, including the drawing figures. Accordingly, the scope of the present invention is defined by the appended claims rather than the foregoing description.

What is claimed is:

1. A method of displaying healthcare-related information on a viewing window in a computer system, the method comprising:
    obtaining a background color used for the display of healthcare-related information in the viewing window;
    calculating a watermark color distinguishable from the background color when displayed in the viewing window such that the watermark is viewable by the human eye; and
    displaying a watermark, for viewing by a user, in the calculated color in the viewing window, the watermark overlaying the healthcare-related information, wherein the watermark and the healthcare-related information are simultaneously readable.

2. The method of claim 1, wherein the watermark is a patient identifying indicia.

3. The method of claim 2, wherein the calculating step includes varying the watermark color according to an intensity value.

4. The method of claim 3, wherein the intensity value is used to adjust the luminescence value of the background color.

5. The method of claim 3, wherein the intensity value is obtained from a user.

6. The method of claim 2, wherein the patient identifying indicia is one of a patient name, a medical record number and a patient location.

7. One or more computer storage media having computer-executable instructions for performing the method recited in claim 1.

8. The method of claim 1, wherein the viewing window is divided into multiple viewing windows, the method further comprising determining whether a digital watermark is desired for any of the multiple viewing windows, and if so displaying a watermark on each of the determined viewing windows.

9. The method of claim 8, wherein the obtaining step includes obtaining the background color for each of the multiple viewing windows needing a watermark and wherein the calculating step is performed for each of the windows needing a watermark.

10. A method in a computer system for displaying healthcare-related information, comprising:
    displaying healthcare-related information on a graphical user interface; and
    displaying a digital watermark of patient identifying indicia on the graphical user interface in a form viewable by the human eye, the watermark overlaying the displayed healthcare-related information.

11. The method of claim 10, further comprising adjusting the color of the digital watermark according to an intensity value.

12. The method of claim 11, further comprising cycling the text of the digital watermark according to a supplied schedule.

13. The method of claim 12, wherein the schedule is user-configurable.

14. A computer system for displaying healthcare-related information, the system comprising:
    a healthcare-related software application component configured to display healthcare-related data; and
    a watermark generation component configured to supply a digital watermark of patient identifying indicia viewable to the human eye, to couple the patient identity with the healthcare-related data, the digital watermark overlaying the healthcare-related data, wherein the digital watermark and the healthcare-related data are simultaneously readable, and further wherein the software application component and the watermark generation component reside on one or more computing devices.

15. The computer system of claim 14, wherein the watermark generation component includes a watermark subject matter determinant component and a color determinant component.

16. The computer system of claim 15, further comprising a rendering component for rendering the healthcare-related data and the watermark on the display, wherein the rendering component resides on the one or more computing devices.

* * * * *